United States Patent [19]
Smith et al.

[11] 3,982,307
[45] Sept. 28, 1976

[54] FABRIC CLAMP

[75] Inventors: Gordon E. Smith, Sun Prairie;
Donald L. Evans, Lake Windsor, both of Wis.

[73] Assignee: Med-Pro, Ltd., Sun Prairie, Wis.

[22] Filed: Feb. 4, 1976

[21] Appl. No.: 655,202

[52] U.S. Cl. .......................... 24/255 SL; 24/137 R
[51] Int. Cl.² .................................. A44B 21/00
[58] Field of Search..... 24/255 SL, 249 SL, 248 SL, 24/255 G, 172 GP; 132/48; 128/321, 346

[56] References Cited
UNITED STATES PATENTS

| | | | |
|---|---|---|---|
| 3,604,071 | 9/1971 | Reimels | 24/248 SL |
| 3,629,912 | 12/1971 | Klopp | 24/255 SL |

*Primary Examiner*—Bernard A. Gelak
*Attorney, Agent, or Firm*—Theodore J. Long; John M. Winter; Harry C. Engstrom

[57] ABSTRACT

A fabric clamp suitable for holding together pieces of fabric, such as surgical drapes, towels and the like, which is relatively compact and inexpensive. The clamp has two resilient arcuate members which are joined together at one end of each member with the arcuate members respectively having convex and concave jaws at their other ends. Latch members extending inward from the arcuate members engage when the clamp is pressed together to maintain the jaws in engagement. Release of the latch members is accomplished by laterally displacing the arcuate members of the clamp. The clamp may have multiple closed clamping positions, and finger members may be provided which are formed on the interior of the arcuate members in position to grasp a tube or other object therebetween when the clamp is closed.

14 Claims, 9 Drawing Figures

FABRIC CLAMP

BACKGROUND OF THE INVENTION

1. Field of the Invention

This invention pertains generally to clamps for holding together pieces of fabric such as surgical drapes and the like.

2. Description of the Prior Art

It is a common practice during surgical procedures to provide cloth towels or disposable absorbent fabrics to absorb body fluids and to protect the area surrounding the incision. Such fabric protection is commonly referred to as a surgical drape, and the drapes must be attached together and held around the incision. The most common method of attaching and fixedly holding the surgical drapes has been to pin the drapes together using metal pins or metal clamps, both of which must be sterilized prior to the operation. Such metal fasteners are expensive and often are lost when the surgical drapes are disposed of or are collected for laundering. In addition, the sterilization of such clamps and other fasteners before each operation adds significantly to the expense of their use.

The problems associated with the use of clips to hold together clothing, bedding and the like around human beings, particularly small children and babies, is well knonw. While the safety pin is widely used as an effective fastener for such things as baby clothing, bedding and so forth, and is often used in hospital situations for pinning together bedding and for attaching tubes and the like in the vicinity of a patient, these pins still present the possibility of springing open and injuring the user. Safety pins additionally present the possibility of being swallowed by a small child. Prior metal or plastic clamps developed to replace safety pins have had limited success because of their size, weight, cost, or difficulty of operation.

SUMMARY OF THE INVENTION

We have invented a fabric clamp which can be used to clip together and securely hold fabric material such as surgical drapes, and can also be used in other situations where fabric is to be held together. Such situations include the securing of bedding in baby cribs and the attachment of tubes, wires, and the like to the beds of hospital patients. Our fabric clamp may also be used in other applications where it is desired to clamp fabric together, as, for example, the pinning and holding of clothes on a line or a rack. Our fabric clamp may be easily sterilized and packaged to remain sterile until time of use in the operating room, and is inexpensive enough to be discarded or used for non-surgical purposes after first use.

Our fabric clamp has two arcuate members joined together integrally at one common end thereof and positioned in outwardly bowed relationship. The two arcuate members each have a free end, which ends are in normally spaced relation when the clamp is in its open or unstressed position. The free end of one of the arcuate members (female member) has a concave surfaced jaw formed thereon, with transverse grooves and ridges preferably being formed in the concave surface. The free end of the other of the arcuate members (male member) has a convex surfaced jaw formed on the end thereof, which also preferably has transverse ridges formed therein. The convex surfaced jaw is adapted to mate with and engage the grooved concave surfaced jaw to securely hold a fabric or other material which is between the surfaces of the jaws.

A first latch member is preferably formed integrally with and extends inwardly from one of the arcuate members and has at least one longitudinal projection thereon, and a second latch member is preferably formed integrally with and extends inwardly from the other of the arcuate members. The second latch member also has a projection thereon which projects in a longitudinal direction opposite to that of the projection on the first latch member, thereby allowing the projections on the first and second latch members to overlap each other in ratchet fashion when the arcuate members are pressed toward each other. The two latch members thus interlock and hold the mating convex and concave surfaced jaws of the arcuate members firmly pressed together to retain any material between the jaws in the desired position.

The arcuate members are formed of a tough and resilient material which allows the arcuate members to be resiliently displaced toward one another as previously described, and also laterally with respect to one another. This flexibility of the arcuate members allow the interlocked latch members to be easily disengaged. The jaws and the longitudinal projections of the latch members are laterally unobstructed. Accordingly, the non-joined portions of the two arcuate members may be displaced laterally with respect to each other to allow the projection on one latch member to slip laterally past the projection on the other latch member until they no longer overlap. The clamp is thereby allowed to spring open and release whatever material has been held between the jaws. The laterally extending grooves of the jaws, which aid in the positive engagement of the material while in the closed position, nevertheless also permit lateral displacement of the arcuate members to facilitate disengagement.

One or both of the latch members may have more than one projection thereon in ratchet fashion to allow the degree of pressure applied at the jaws of the clamp to be adjusted. Such additional projections are preferably of a smaller lateral dimension than the first projection on each latch member to facilitate disengagement by lateral displacement.

Our clamp also preferably includes opposed finger members which extend inwardly from each of the arcuate members of the clamp at a position between the latch members and the joint between the arcuate members. Each finger member has an inwardly projecting portion and a cantilever portion extending from the end thereof toward the joint between the arcuate members. The cantilever portions of each of the finger members are in opposed normally spaced relation when the clamp is in its open position. When the clamp is closed the cantilever portions of the finger members will be displaced toward one another to thereby grasp an object such as a tube or line which has been placed therebetween and to resiliently hold such an object. The finger members are preferably formed integrally with the arcuate members and of the same resilient material to thus provide a resilient grasp of any object that is between the finger members.

Finger pads may also be provided on the outer surfaces of the two arcuate members and may have grooves therein to allow the clamp to be more easily grasped and pressed by the fingers of the user.

Further objects, features, and advantages of our invention will be apparent from the following detailed description taken in conjunction with the accompanying drawings showing preferred embodiments of a fabric clamp exemplifying the principles of our invention.

DESCRIPTION OF THE PREFERRED EMBODIMENTS

Figure 1:
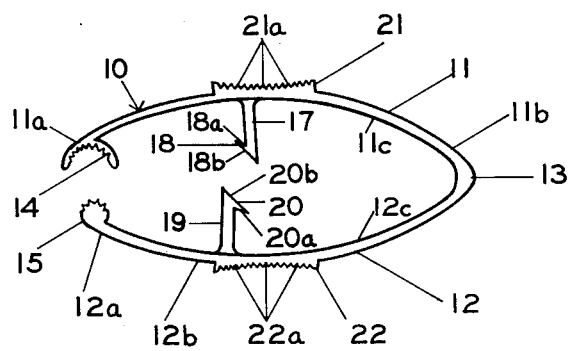
FIG. 1 is a side view of our fabric clamp in an open position.

Referring now more particularly to the drawings, wherein like numerals refer to like parts throughout the several views, an embodiment of our fabric clamp is shown generally at 10 in FIG. 1. The clamp 10 has a first arcuate member 11 and a second arcuate member 12 which are positioned in outwardy bowed relationship to one another, one end of each arcuate member meeting and being integrally joined with a similar end of the other arcuate member at a joint 13. The arcuate member 11 has a free end 11a which is in normally spaced relationship with a free end 12a of the arcuate member 12.

As shown in FIG. 1, the free end 11a of the first arcuate member has a laterally extending concave surfaced jaw 14 thereon which is preferably formed integrally with the first arcuate member, the concave surface of the jaw facing the other free end 12a. The concave jaw 14 preferably has laterally running ridges and grooves formed on the surface thereof. The free end 12a of the second arcuate member has a laterally extending convex surfaced jaw 15 thereon which also is preferably formed integrally with the arcuate member. The convex surfaced jaw preferably has laterally running ridges and grooves formed on its surface. The concave surfaced jaw 14 and convex surfaced jaw 15 respectively form mating female and male members. The concave surfaced jaw 14 and the convex surfaced jaw 15 are maintained in spaced relationship when the fabric clamp is in its unstressed or open position shown in FIG. 1. The arcuate members are preferably formed as an integral unit of a material which is flexible and tough, which can be bent severely without breaking, and which is capable of resiliently returning to substantially its initial configuration.

Figure 2:
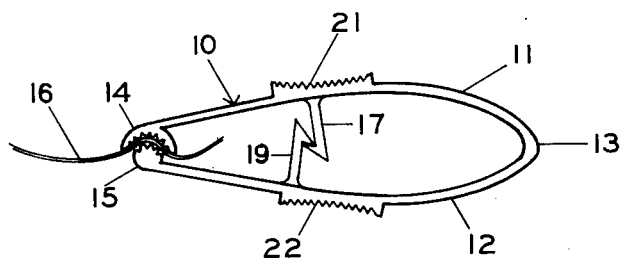
FIG. 2 is a side view of the fabric clamp of FIG. 1 in a closed position engaging a piece of fabric.

Inward pressure on the outside surface 11b of the arcuate member 11 and on the outside surface 12b of the arcuate member 12 causes the jaws 14 and 15 to be displaced toward engagement to a closed mating position such as shown in FIG. 2, to hold one or more thicknesses of fabric 16 or other flexible material between the jaws. The mating lateral grooves and ridges on the surfaces of the jaws aid in the grasping of the fabric, and help to maintain the surfaces of the jaws in firm engagement through a piece of fabric to inhibit longitudinal displacement of the jaws as the arcuate members are pressed inwardly together. However, the grooves do not interfere with lateral displacement of the jaws, which are laterally unobstructed. It may also be noted that the convex surfaced jaw will fit into the concave surfaced jaw 14 to inhibit motion of the jaws relative to one another in a longitudinal dimension, wherein the longitudinal dimension is the dimension of the fabric clamp generally along or parallel to a line running from the joined ends of the arcuate members to the free ends of the arcuate members.

The fabric clamp 10 has a first latch member 17 which is preferably formed integrally with the first arcuate member 11 and extends inwardly therefrom toward the second arcuate member 12. The first latch member 17 has a projection 18 on the end thereof which projects longitudinally from the latch member 17 a short distance toward the open end of the fabric clamp. As shown in FIG. 1, the projection 18 preferably forms a small ratchet-like "hook," with a flat shelf 18a facing the inner surface 11c of the first arcuate member 11, and with an inclined surface 18b facing generally toward the inner surface 12c of the second arcuate member 12. A second latch member 19 is preferably formed integrally with the second arcuate member 12 and extends inwardly therefrom toward the first arcuate member. The second latch member 19 also has ratch-like projection 20 formed on the end thereof which projects longitudinally a short distance toward the joint 13 to form a hook on the end of the latch member 19. The projection 20 is preferably formed as shown in FIG. 1, having a flat shelf 20a which faces the inner surface 12c of the second arcuate members, and an inclined surface 20b which generally faces the inner surface 11c of the first arcuate members. As shown in FIG. 1, the inclined surface 18b of the projection 18 on the first latch member and the inclined surface 20b of the projection 20 on the second latch member are in position to engage each other and slide past each other when the first and second arcuate members of the clamp 10 are displaced toward one another. It is preferable that the latch member 19 be positioned slightly forward of the latch member 17 as shown, to allow the latch members to pass by one another with some, but not excessive, bending.

After the arcuate members of the clamp 10 have been displaced inwardly toward one another a sufficient distance, the shelf 18a on the projection 18 will overlap with the shelf 20a on the projection 20 to thereby engage the first latch member 17 with the second latch member 18 and thus prevent the clamp 10 from springing to its open position. The relationship of the parts in the closed position of the clamp 10 is shown in FIG. 2. It is apparent that the respective attitudes of the latch members 17 and 19 could be reversed without affecting the functioning of our fabric clamp. The latch members could be formed in such reversed positions by having the projection 20 project toward the open ends of the arcuate members and the projection 18 project toward the joint 13, and by positioning the latch 17 forwardly of the latch 19. The projection 18 and the projection 20 are laterally unobstructed to permit lateral displacement of the arcuate members and the engaged latch members, to allow opening the clamp when desired, as described below.

Raised finger pads 21 and 22 are formed integrally with the first arcuate member 11 and the second arcuate member 12 respectively, to allow for convenient grasping of the clamp by fingers of the user. The finger pads 21 and 22 may have grooves 21a and 22a respectively formed therein to allow more positive contact between the pads and the fingers of the user.

Figure 3:
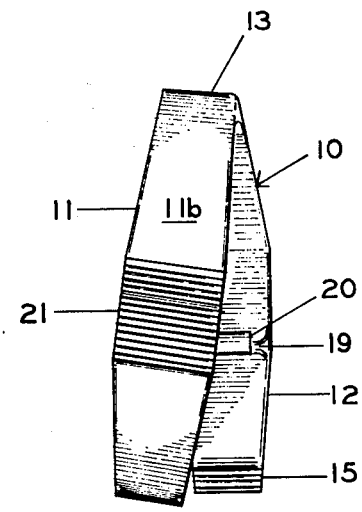
FIG. 3 is a top view of the fabric clamp of FIG. 1, with the arcuate members thereof in lateral displacement to illustrate the release of the clamp.

Release of our fabric clamp 10 from its closed position is easily accomplished by simply laterally displacing the non-joined portions of the first and second arcuate members, causing a torsional rotation of the arcuate members about joint 13, as illustrated in FIG. 3. As previously explained, the jaws 14 and 15 and the latch member projections 18 and 20 are laterally unobstructed to permit relative lateral movement of all engaged surfaces. Once the shelf 18a on the projection 18 has laterally cleared and no longer overlaps and shelf 20a on the projections 20, the first and second arcuate members will be free to spring back to their normally open position. In order to allow release of the clamp by simple lateral displacement of the first and second arcuate members, it is necessary that the material out of which the clamp 10 is made be bendable and resilient, yet tough enough to allow the arcuate members to be substantially displaced without breading or cracing. Examples of such materials which are suitable for the production of our fabric clamp are formed nylon and polypropylene, although other materials having similar properties are also acceptable.

Figure 4:
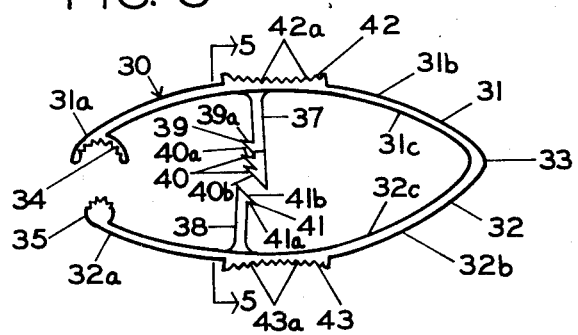
FIG. 4 is a side view of another embodiment of our fabric clamp having multiple closed positions.

Another embodiment of a fabric clamp in accordance with our invention is shown generally at 30 in FIG. 4. The fabric clamp 30 is substantially similar to the fabric clamp 10 shown in FIG. 1, and is made of a resilient materal having the same characteristics described above for the material composing the fabric clamp 10. The fabric clamp 30 has a first arcuate member 31 and a secondarcuate member 32 in outwardly bowed relationship, with one end of each arcuate member being integrally joined with a similar end of the other arcuate member at a joint 33. The first arcuate member has a laterally extending concave surfaced jaw 34 at the free end 31a thereof, and the second arcuate member 32 has a laterally extending convex surfaced jaw 35 at its free end 32a. The surface of the concave jaw 34 preferably has laterally running ridges and grooves formed thereon while the surface of the convex jaw 35 preferably also has laterally running ridges and grooves formed thereon. These jaws are engaged together by pressing on the outside surfaces 31b and 32b of the arcuate members 31 and 32 respectively, and thus displacing the first and second arcuate members together in a manner as described above for the fabric clamp 10.

Figure 5:
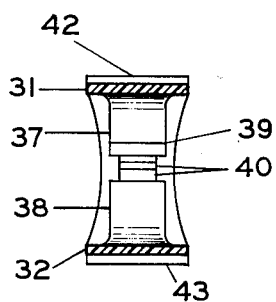
FIG. 5 is a cross sectional view of the fabric clamp of FIG. 4 taken along section line 5—5 of FIG. 4.

A first latch member 37 is formed integrally with and extends inwardly from the first arcuate member 31 toward the second arcuate member 32. A second latch member 38 is formed integrally with the second arcuate member 32 and extends inwardly therefrom toward the first arcuate member 31. The first latch member 37 has a first ratchet-like projection 39 thereon which projects a short distance longitudinally toward the open end of the clamp 30, in the same manner as previously described projection 18 of FIG. 1. The first latch member 31 also has additional toothed projections 40 spaced inwardly from the first projection which also similarly project longitudinally toward the open end of the clamp 30. As best shown in the cross sectional view in FIG. 5, the additional projections 40 are of a smaller lateral dimension than the first projection 39.

The projection 39 has a flat shelf 39a facing the inner surface 31c of the first arcuate member 31. The additional projections 40 also each have a shelf 40a generally facing the inner surface 31c and an inclined surface 40b generally facing the second arcuate member 32.

The second latch member 38 also has a ratchet-like projection 41 which projects longitudinally from the second latch member a short distance toward the joint 33. As shown in FIG. 4, the projection 41 has a flat shelf 41a facing the inner surface 32c of the arcuate member 32, and an inclined surface 41b which generally faces the first arcuate member 31.

The fabric clamp 30 may be closed and the arcuate members displaced toward each other by applying pressure to the outside surfaces 31b and 32b of the first and second arcuate members respectively. The projection 41 on the second latch member first slides over the innermost additional projection 40 on the latch member 37 until the shelf 41a of the projection 41 and the shelf 40a of the innermost projection 40 overlap. In this position, the jaws 34 and 35 will be pressed together over a piece of fabric with a light amount of pressure. Additional pressure may be applied between the jaws 34 and 35 by pressing together the arcuate members until the projection 41 engages the next innermost additional projection 40 on the first latch member 37. In this position, somewhat more pressure will be applied between the jaws 34 and 35. Finally, the arcuate members 31 and 32 may be displaced sufficiently toward one another that the projection 41 slips over and engages the first projection 39 on the first latch member 37 to securely hold whatever fabric is between the jaws 34 and 35 with the maximum amount of pressure. It is apparent that additional projections 40 could be provided on the latch member 37 to provide a selected number of adjustable settings of the pressure between the jaws 34 and 35. Because the additional projections 40 are not as wide in lateral dimension as the first projection 39, disengagement of the projection 41 with one of the additional projections 40 may be accomplished with a smaller lateral displacement of the first arcuate member from the second arcuate member than would be required if the projection 41 was being disengaged laterally from the first projection 39 on the first latch member 37. The jaws 34 and 35 and projections 39, 40 and 41 are laterally unobstructed to permit lateral displacement of the arcuate members 31 and 32 to open the clamp 30.

As shown in FIG. 4, the fabric clamp 30 also preferably was a finger pad 42 formed integrally with the first arcuate member 31 and a finger pad 43 which is formed integrally with the second arcuate member 32. Again, the finger pads 42 and 43 may have grooves 42a and 43a respectively formed therein to facilitate grasping of the pads by fingers of the user.

Figure 6:
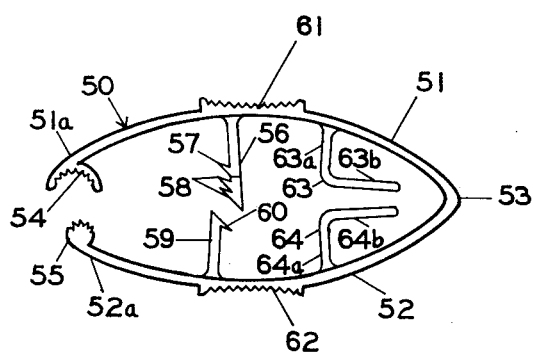
FIG. 6 is a side view of another embodiment of our fabric clamp having clasping finger members projecting inwardly from the arcuate members of the clamp.
Figure 7:
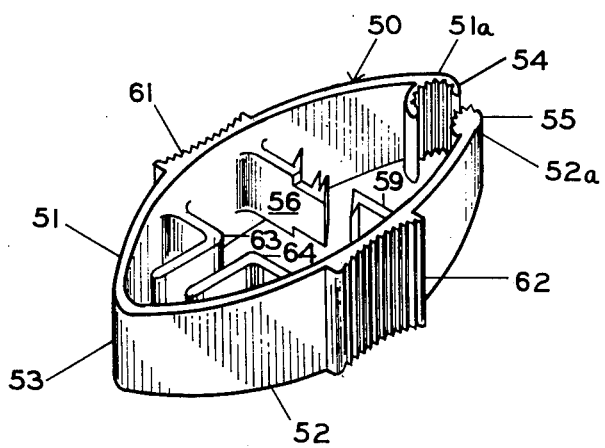
FIG. 7 is a perspective view of the fabric clamp of FIG. 6.

Another embodiment of our fabric clamp is shown generally at 50 in FIGS. 6 and 7. The fabric clamp 50 is substantially similar to the fabric clamp 30 shown in FIG. 4, and has a first arcuate member 51 and second arcuate member 52 positioned in outwardly bowed relationship, with one end of each arcuate member being integrally joined with a similar end of the other arcuate member at a joint 53. The free end 51a of the first arcuate member has a lateraly extending concave surfaced jaw 54 with laterally running ridges and grooves preferably formed thereon, and the free end of the second arcuate member has a laterally extending convex surfaced jaw 55 with laterally running ridges and grooves preferably formed on the surface thereof. A first latch member 56 is formed integrally with and extends inwardly from the first arcuate member and has a first longitudinally extending ratch-like projection 57 thereon and additional longitudinal projections 58. A second latch member 59 is formed integrally with and extends inwardly from the second arcuate member and has a similar longitudinally projecting projection 60 on the end thereof. The projection 57 and the additional projections 58 on the first latch member 56 engage with and disengage from the projection 60 on the second latch member 59 in the manner described above for the latch members on the clamp 30. The fabric clamp 50 also preferably has a finger pad 61 with grooves therein, which is formed integrally with the first arcuate member, and a finger pad 62 with grooves therein formed integrally with the second arcuate member.

It is often desirable to provide a means to clasp and hold tubes, wires and so forth in the vicinity of patients in a hospital bed without damaging the tubes or wires. Often these tubes and wires are pinned with safety pins to the bedding of the patient, or to other convenient points of attachment. The fabric clamp 50 is adapted to conveniently hold such tubes and wires, having first and second finger members 63 and 64 which are preferably formed integrally with the first and second arcuate members respectively, and which extend inwardly toward each other between the arcuate members. As best shown in FIG. 6, the first finger member 63 has an inwardly extending portion 63a and a cantilever portion 63b which extends rearwardly from the end of the inwardly extending portion toward the joint 53. Similarly, the second finger member 64 has an inwardly extending portion 64a and a cantilever portion 64b extending therefrom rearwardly toward the joint 53. The cantilever portions 63b and 64b of the finger members are thus maintained in normally spaced relation when the clamp 50 is in its open position as shown in FIGS. 6 and 7. It will be appreciated however, that when the clamp 50 is closed and the latch member 59 engages with the latch 56, the cantilever portion 63b and the cantilever portion 64b will be displaced toward one another to an extent determined by the engagement of the projection 60 on the latch member 59 with either the additional projections 58 or the first projection 57 on the first latch member 56, thereby allowing the pressure that is applied on any object grasped between the cantilever portions 63b and 64b to be adjusted. The finger members are preferably made of the same resilient material as the arcuate members, and the flexibility of the cantilever portions allows the object grasped therebetween to be resiliently held without imposing excessive pressure on such object. The relationship of the finger members 63 and 64 with the remaining portions of the clamp 50 is illustrated in perspective in FIG. 7. It is apparent that the finger members 63 and 64 may be utilized for purposed other than holding tubes and wires on patients' bedding, and for example, may be utilized to grasp a line or bar to hold the clamp 50 in place thereon while the jaws 54 and 55 are grasping a piece of fabric such as clothing. It is also apparent that finger members substantially identical to the finger members 63 and 64 may be formed on and utilized with the fabric clamp of our invention shown generally at 10 in FIGS. 1, 2 and 3.

Figure 8:
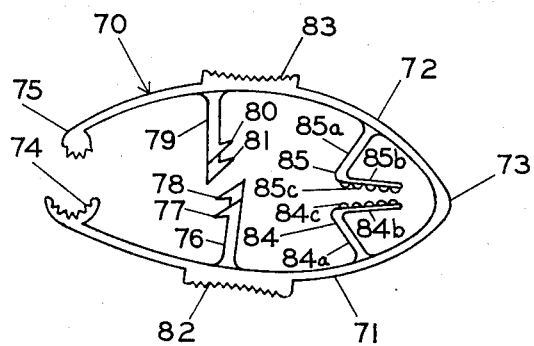
FIG. 8 is a side view of another embodiment of our fabric clamp having multiple closed positions and clasping finger members.

A further embodiment of our fabric clamp is shown generally at 70 in FIG. 8. The clamp 70 has outwardly bowed arcuate members 71 and 72 integrally joined at a joint 73, a concave jaw 74 having laterally running ridges and grooves therein formed on the free end of the arcuate member 71 and a convex jaw 75 with laterally running ridges and grooves therein formed on the free end of the arcuate member 72.

A first latch member 76 extends inwardly from attachment with the first arcuate member 71. The latch member 76 has a first longitudinal projection 77 and a second longitudinal projection 78 thereon, with the second projection 78 being of smaller lateral dimension than the first projection 77.

A second latch member 79 extends inwardly from attachment with the second arcuate member 72. The latch member 79 has a first longitudinal projection 80 and a second longitudinal projection 81 thereon, with the second projection 81 being of smaller lateral dimension than the first projection 80. The projections 80 and 81 extend in a direction opposite to that in which the projections 77 and 78 extend, and the latch members 76 and 79 are positioned so that the projections on the respective latch members will engage each other when the arcuate members are pressed toward one another.

Finger pads 82 and 83 are provided as shown on the outer surfaces of the arcuate members 71 and 72 respectively.

A first finger member 84 is attached to and extends inwardly from the first arcuate member 71. The finger member 84 has an inwardly extending portion 84a and a cantilever portion 84b extending therefrom toward the joint 73. The inner surface of the cantilever portion 84b has a series of small knobs 84c projecting therefrom to aid in the grasping of an object by the finger member. A second finger member 85 is attached to and extends inwardly from the second arcuate member 72, and similarly has an inwardly extending portion 85a, a cantilever portion 85b, and a series of small knobs 85c on the inner surface of the cantilever portion.

Figure 9:
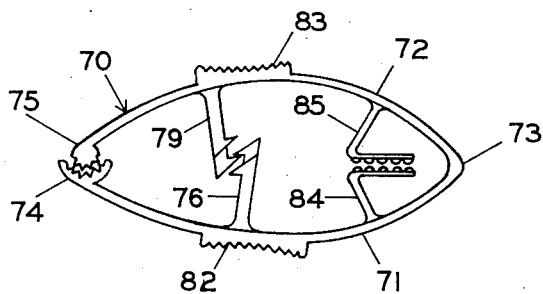
FIG. 9 is a side view of the fabric clamp of FIG. 8 in its first closed position.

The materials, construction and operation of the fabric clamp 70 is similar to the fabric clamp 50 as described above. However, as shown in FIG. 9, the fabric clamp 70 has a first closed position in which only the longitudinal projections 78 and 81 are in engagement. Release of the fabric clamp from this first closed position is achieved with a smaller lateral displacement of the arcuate members 71 and 72 than is required for release from a second closed position wherein projections 78 and 80 are in engagement and 77 and 81 are in engagement. Still greater lateral displacement is required for release from a third closed position wherein projections 77 and 80 are in engagement.

It is understood that our invention is not confined to the particular construction and arrangement of parts herein illustrated and described, but embraces all such modified forms thereof as come within the scope of the following claims.

We claim:
1. A fabric clamp comprising:
   a. two arcuate members having fixed ends joined together, said arcuate members extending from said fixed ends in spaced outwardly bowed relation to free ends positioned in normally spaced relation, said arcuate members being formed of a flexible and resilient material to allow them to be displaced toward one another to cause engagement of said free ends and to allow the non-joined portions of said arcuate members to be displaced laterally with respect to one another;
b. a concave surfaced jaw on the free end of one of said arcuate members, the concave surface of said jaw facing said other free end;
c. a convex surfaced jaw on the free end of the other of said arcuate members, the convex surface of said jaw facing said concaved surfaced jaw;
d. a first latch member extending inwardly from one of said arcuate members and having a longitudinal projection on the end thereof; and
e. a second latch member extending inwardly from the other of said arcuate members and having a longitudinal projection on the end thereof in position to overlap and engage with the projection on said first latch member when said arcuate members are displaced toward each other to a closed position to maintain said concave and convex surfaced jaws in mating engagement;
f. said jaws and said latch member longitudinal projections being laterally unobstructed whereby said jaws may be released to their normally open position by laterally displacing said arcuate members until said projections on said latch members are no longer in overlapping engagement.

2. The fabric clamp as specified in claim 1 wherein said convex surfaced jaw and said concave surfaced jaw have laterally running ridges and grooves formed in the respective surfaces thereof.

3. The fabric clamp as specified in claim 1 wherein each of said arcuate members has a finger pad on the outside surface thereof having grooves therein for engagement by the fingers of a user.

4. The fabric clamp as specified in claim 1 wherein said arcuate members are formed of nylon.

5. The fabric clamp as specified in claim 1 wherein said arcuate members are formed of polypropylene.

6. The fabric clamp as specified in claim 1 including a first finger member having a portion thereof extending inwardly from one said arcuate member and a cantilever portion extending therefrom rearwardly toward the joined fixed ends of said arcuate members, and also including a second finger member having a portion thereof which extends inwardly from the other said arcuate member and a cantilever portion which extends therefrom rearwardly toward the joined ends of said arcuate members, and wherein said cantilever portions of said finger members are in normally spaced relationship when said clamp is in its open position and are displaced toward one another to grasp an object therebetween when said clamp is moved to its closed position.

7. A fabric clamp comprising:
a. two arcuate members joined together at one end of each said arcuate member in outwardly bowed relationship, said arcuate members each having a free end with said free ends being in normally spaced relationship, said arcuate members being formed of a flexible and resilient material to allow them to be displaced toward one another to cause engagement of said free ends and to allow the non-joined portions of said arcuate members to be displaced laterally with respect to one another;
b. a concave surfaced jaw on the free end of one of said arcuate members, the concave surface of said jaw facing said other free end;
c. a convex surfaced jaw on the free end of the other of said arcuate members, the convex surface of said jaw facing said concave surfaced jaw;
d. a first latch member extending inwardly from one of said arcuate members and having a first longitudinal projection thereon and at least one additional longitudinal projection thereon spaced inwardly from said first projection;
e. a second latch member extending inwardly from the other of said arcuate members and having at least one longitudinal projection thereon, said second latch member projection being in position to overlap and engage with said first latch member projection and said additional projection when said arcuate members are displaced toward each other to maintain said jaws in mating engagement, whereby the engagement of said second latch member projection with either of said first latch member projections depends on the extent to which said arcuate members are displaced toward one another;
f. said jaws and said latch member longitudinal projections being laterally unobstructed whereby said jaws may be released to their normally open position by laterally displacing said arcuate members until said projections on said latch members are no longer in overlapping engagement.

8. The fabric clamp as specified in claim 7 wherein the first latch member additional longitudinal projection is of smaller lateral dimension than the first longitudinal projection, whereby the second latch member longitudinal projection may be disengaged from said additional projection on said first latch member with less lateral displacement of said arcuate members than is required to disengage said second latch member projection from the first latch member first projection.

9. The fabric clamp as specified in claim 8 wherein the second latch member has at least one additional longitudinal projection spaced inwardly from the first projection thereon, and wherein said additional projection is of smaller lateral dimension than the first projection thereon.

10. The fabric clamp specified in claim 7 wherein each of said arcuate members has a finger pad on the outside surface thereof having grooves therein for engagement by the fingers of a user.

11. The fabric clamp specified in claim 7 wherein said convex surfaced jaw and said concave surfaced jaw each have laterally running ridges and grooves formed in the respective surfaces thereof.

12. The fabric clamp specified in claim 7 wherein said arcuate members are formed of nylon.

13. The fabric clamp specified in claim 7 wherein said arcuate members are formed of polypropylene.

14. The fabric clamp specified in claim 7 including a first finger member having a portion thereof extending inwardy from one of said arcuate members and a cantilever portion extending therefrom rearwardly toward the joined ends of said arcuate members, and also including a second finger member having a portion thereof which extends inwardly from the other of said arcuate members and a cantilever portion which extends therefrom rearwardly towards the joined ends of said arcuate members, said cantilever portions of said finger members being in normally spaced relationship when said clamp is in its open position and whereby said cantilever portions are displaced toward one another to grasp an object therebetween when said clamp is moved to its closed position.

* * * * *